US012702831B2

(12) United States Patent
Chiapetta et al.

(10) Patent No.: US 12,702,831 B2
(45) Date of Patent: Aug. 11, 2026

(54) SYSTEMS AND METHODS TO MANAGE MICROCURRENT THERAPY DOSE

(71) Applicant: i-Lumen Scientific, Inc., Bloomington, MN (US)

(72) Inventors: James R. Chiapetta, Delano, MN (US); Michael A. Moffitt, Delano, MN (US)

(73) Assignee: i-Lumen Scientific, Inc., Bloomington, MN (US)

( * ) Notice: Subject to any disclaimer, the term of this patent is extended or adjusted under 35 U.S.C. 154(b) by 275 days.

(21) Appl. No.: 18/478,460

(22) Filed: Sep. 29, 2023

(65) Prior Publication Data

US 2024/0108897 A1 Apr. 4, 2024

Related U.S. Application Data

(60) Provisional application No. 63/411,562, filed on Sep. 29, 2022.

(51) Int. Cl.
*A61N 1/36* (2006.01)

(52) U.S. Cl.
CPC ..... *A61N 1/36031* (2017.08); *A61N 1/36046* (2013.01)

(58) Field of Classification Search
CPC ........................ A61N 1/36031; A61N 1/36046
See application file for complete search history.

(56) References Cited

U.S. PATENT DOCUMENTS 2,283,752 A 5/1942 Gonsett
2,527,947 A 10/1950 Loos
2,760,483 A 8/1956 Tassicker
3,376,870 A 4/1968 Yamamoto et al.
3,669,119 A 6/1972 Symmes
D246,529 S 11/1977 Willard
4,162,542 A 7/1979 Frank
D280,670 S 9/1985 Fireman
4,551,149 A 11/1985 Scairra
(Continued)

FOREIGN PATENT DOCUMENTS

CN 1096460 A 12/1994
DE 202012003100 U1 10/2012
(Continued)

OTHER PUBLICATIONS

Chlaihawi et al; "Development of Printed and Flexible Dry ECG Electrodes", Sensing and Bio-Sensing Research, vol. 20, pp. 9-15, 2018.

(Continued)

*Primary Examiner* — Brian T Gedeon
(74) *Attorney, Agent, or Firm* — Fox Rothschild LLP

(57) ABSTRACT

Methods, apparatuses and systems for ophthalmic therapy. Electrical therapy delivery characteristics are determined using a testing or calibration phase and a patient's known disease state. Expected values for phosphene thresholds in the patient's eye are used along with measurements characterizing a relationship between therapy output from electrodes near the eye to the energy that is actually received at the eye, such as by corneal measurements. The result may include a determination of therapy delivery targets and/or an estimate of the patient's disease state.

9 Claims, 5 Drawing Sheets

(56) References Cited

U.S. PATENT DOCUMENTS 4,614,193 A 9/1986 Liss et al.
4,628,933 A 12/1986 Michelson
4,664,117 A 5/1987 Beck
4,712,558 A 12/1987 Kidd et al.
4,979,811 A 12/1990 Boyer
5,024,223 A 6/1991 Chow
5,109,844 A 5/1992 De Juan et al.
5,147,284 A 9/1992 Fedorov et al.
5,154,174 A 10/1992 Hawlina
5,193,540 A 3/1993 Schulman et al.
5,263,200 A 11/1993 Miller
5,522,864 A 6/1996 Wallace et al.
5,556,423 A 9/1996 Chow et al.
5,597,381 A 1/1997 Rizzo, III
5,643,330 A 7/1997 Holsheimer et al.
5,836,996 A 11/1998 Doorish
5,843,147 A 12/1998 Testerman et al.
5,865,839 A 2/1999 Doorish
5,873,901 A 2/1999 Wu et al.
5,895,415 A 4/1999 Chow et al.
5,935,155 A 8/1999 Humayun et al.
5,944,747 A 8/1999 Greenberg et al.
6,007,532 A 12/1999 Netherly
D421,124 S 2/2000 Yavitz
6,035,236 A 3/2000 Jarding et al.
D425,623 S 5/2000 Funk
D429,817 S 8/2000 Banks
6,101,411 A 8/2000 Newsome
6,131,208 A 10/2000 Banks
6,154,671 A 11/2000 Parel et al.
D440,660 S 4/2001 Sternberg
6,230,057 B1 5/2001 Chow et al.
D444,561 S 7/2001 Stein
6,275,735 B1 8/2001 Jarding et al.
6,282,449 B1 8/2001 Kamerling et al.
6,306,075 B1 10/2001 Shadduck
6,324,429 B1 11/2001 Shire et al.
6,389,317 B1 5/2002 Chow et al.
6,400,989 B1 6/2002 Eckmiller
6,408,211 B1 6/2002 Powell
6,424,864 B1 7/2002 Matsuura
6,442,431 B1 8/2002 Veraart et al.
6,458,157 B1 10/2002 Suaning
6,515,227 B1 2/2003 Massey et al.
6,611,716 B2 8/2003 Chow et al.
6,755,530 B1 6/2004 Loftus et al.
6,792,314 B2 9/2004 Byers et al.
6,976,998 B2 12/2005 Rizzo et al.
6,990,377 B2 1/2006 Gliner et al.
7,001,608 B2 2/2006 Fishman et al.
7,003,354 B2 2/2006 Chow et al.
7,006,873 B2 2/2006 Chow et al.
7,031,776 B2 4/2006 Chow et al.
7,037,943 B2 5/2006 Peyman
7,043,308 B2 5/2006 Cohen
7,047,080 B2 5/2006 Palanker et al.
7,058,455 B2 6/2006 Huie, Jr. et al.
7,067,327 B2 6/2006 Wu et al.
7,130,693 B1 10/2006 Montalbo
7,139,612 B2 11/2006 Chow et al.
7,146,209 B2 12/2006 Gross et al.
7,147,865 B2 12/2006 Fishman et al.
7,158,834 B2 1/2007 Paul, Jr.
7,158,836 B2 1/2007 Suzuki
7,248,928 B2 7/2007 Yagi
7,251,528 B2 7/2007 Harold
7,306,621 B1 12/2007 Halla et al.
7,321,796 B2 1/2008 Fink et al.
7,337,008 B2 2/2008 Terasawa et al.
7,398,124 B2 7/2008 Fujikado et al.
7,400,021 B2 7/2008 Wu et al.
7,447,547 B2 11/2008 Palanker
7,447,548 B2 11/2008 Eckmiller
7,458,456 B2 12/2008 Hogan et al.
7,556,621 B2 7/2009 Palanker et al.
7,877,148 B2 1/2011 Chowdhury et al.
7,883,535 B2 2/2011 Cantin et al.
7,974,699 B2 7/2011 Tano et al.
7,979,134 B2 7/2011 Chow et al.
7,981,062 B2 7/2011 Chow et al.
8,000,804 B1 8/2011 Wessendorf et al.
8,039,445 B2 10/2011 Behar-Cohen et al.
8,070,688 B2 12/2011 Livne et al.
8,190,266 B2 5/2012 Ameri et al.
8,197,539 B2 6/2012 Nasiatka et al.
8,260,428 B2 9/2012 Fink et al.
8,265,764 B2 9/2012 Tano et al.
8,306,626 B2 11/2012 Chow et al.
8,377,120 B2 2/2013 Lipshitz et al.
8,396,561 B2 3/2013 Pezaris et al.
8,396,562 B2 3/2013 Ameri et al.
8,398,692 B2 3/2013 Deisseroth et al.
8,433,417 B2 4/2013 Flood
8,478,415 B1 7/2013 Halla et al.
8,515,548 B2 8/2013 Rofougaran et al.
8,612,002 B2 12/2013 Faltys et al.
8,634,923 B2 1/2014 Sharpee et al.
8,639,345 B2 1/2014 Eipper et al.
8,691,877 B2 4/2014 Yun et al.
8,700,167 B2 4/2014 Sabel
8,725,266 B2 5/2014 Olson et al.
8,731,683 B2 5/2014 Lindenthaler
8,734,513 B2 5/2014 Wu et al.
8,771,349 B2 7/2014 Schachar
8,788,041 B2 7/2014 Yun et al.
8,801,942 B2 8/2014 Scorsone et al.
8,824,156 B2 9/2014 Tai et al.
8,852,290 B2 10/2014 Rowley et al.
8,864,805 B2 10/2014 Deisseroth et al.
8,868,202 B2 10/2014 Della Santina et al.
8,903,495 B2 12/2014 Greenberg et al.
8,909,340 B2 12/2014 Yun
8,918,186 B2 12/2014 Tiedtke
8,918,188 B2 12/2014 Tiedtke
8,972,004 B2 3/2015 Simon et al.
9,002,463 B2 4/2015 Tiedtke
9,037,251 B2 5/2015 Narayan et al.
9,037,252 B2 5/2015 Tiedtke
9,037,255 B2 5/2015 Rocke et al.
9,078,743 B2 7/2015 Tai et al.
9,079,042 B2 7/2015 Tiedtke et al.
9,125,734 B2 9/2015 Keller et al.
9,144,608 B2 9/2015 Olson et al.
9,162,060 B2 10/2015 Wrobel et al.
9,162,061 B2 10/2015 Barnes
9,180,309 B2 11/2015 Nirenberg et al.
9,186,523 B1 11/2015 Zolli
9,187,745 B2 11/2015 Deisseroth et al.
9,199,080 B2 12/2015 Gekeler et al.
9,220,634 B2 12/2015 Nirenberg
9,220,894 B1 12/2015 Zhu
9,233,026 B2 1/2016 Ziemeck et al.
9,233,258 B2 1/2016 Simon et al.
9,242,067 B2 1/2016 Shore et al.
9,302,103 B1 4/2016 Nirenberg
9,322,713 B2 4/2016 Narayan et al.
9,326,887 B2 5/2016 Yun
9,339,650 B2 5/2016 Rezai et al.
9,345,568 B2 5/2016 Cho et al.
9,370,348 B2 6/2016 Tally et al.
9,381,355 B2 7/2016 Khraiche et al.
9,403,001 B2 8/2016 Simon et al.
9,452,289 B2 9/2016 Chichilnisky et al.
9,456,836 B2 10/2016 Boling et al.
9,468,760 B1 10/2016 Lin
9,498,380 B2 11/2016 Berdahl et al.
9,630,013 B2 4/2017 Bachinski et al.
9,636,212 B2 5/2017 Tiedtke et al.
9,682,232 B2 6/2017 Shore et al.
9,687,652 B2 6/2017 Franke et al.
9,697,746 B2 7/2017 Barnes et al.
9,737,710 B2 8/2017 Fan
9,737,711 B2 8/2017 Twyford et al.
9,789,312 B2 10/2017 Fukuma et al.

(56) References Cited

U.S. PATENT DOCUMENTS 9,795,787 B2 10/2017 Cho et al.
9,821,003 B2 11/2017 Yun
9,821,159 B2 11/2017 Ackermann et al.
9,844,459 B2 12/2017 Badawi
9,867,988 B2 1/2018 Fink et al.
9,884,180 B1 2/2018 Ho et al.
9,895,529 B2 2/2018 Tiedtke
9,925,373 B2 3/2018 Nirenberg
9,931,506 B2 4/2018 Chung et al.
9,937,346 B2 4/2018 Lineaweaver et al.
9,950,153 B2 4/2018 Wagner et al.
9,956,425 B2 5/2018 Peyman
9,962,540 B2 5/2018 Picaud et al.
9,962,558 B2 5/2018 Peyman
9,980,388 B2 5/2018 Tai et al.
9,990,861 B2 6/2018 Chichilnisky et al.
10,010,364 B2 7/2018 Harrington
10,071,251 B2 9/2018 Bachinski et al.
10,112,048 B2 10/2018 Franke et al.
10,129,647 B2 11/2018 Seo et al.
10,347,050 B1 7/2019 Wang et al.
11,305,118 B2 4/2022 Rockley et al.
11,338,139 B2 5/2022 Rockley et al.
11,471,680 B2 10/2022 Chiapetta et al.
11,511,112 B2 11/2022 Mullins et al.
2003/0158588 A1 8/2003 Rizzo et al.
2003/0233135 A1 12/2003 Yee
2003/0233137 A1 12/2003 Paul, Jr.
2004/0106965 A1 6/2004 Chow
2004/0176820 A1 9/2004 Paul, Jr.
2005/0004625 A1 1/2005 Chow
2005/0049578 A1 3/2005 Tu et al.
2005/0137649 A1 6/2005 Paul, Jr.
2006/0142818 A1 6/2006 Chow et al.
2007/0093877 A1 4/2007 Beecham et al.
2008/0171929 A1 7/2008 Katims
2008/0194531 A1 8/2008 Steer et al.
2009/0217938 A1 9/2009 Rabe et al.
2009/0287276 A1 11/2009 Greenberg et al.
2011/0081333 A1 4/2011 Shantha et al.
2012/0123501 A1 5/2012 Greenberg et al.
2013/0053733 A1 2/2013 Korb et al.
2013/0066396 A1 3/2013 Gekeler et al.
2013/0184782 A1 7/2013 Eipper et al.
2014/0257433 A1 9/2014 Ackermann et al.
2014/0277435 A1 9/2014 Gefen
2015/0039067 A1 2/2015 Greenberg et al.
2016/0051439 A1 2/2016 Brown et al.
2016/0317474 A1 11/2016 Aung et al.
2017/0266445 A1 9/2017 O'Clock
2017/0319093 A1* 11/2017 Stewart .................... A61N 2/02
2018/0064935 A1 3/2018 Leonhardt et al.
2018/0228237 A1 8/2018 Zhang et al.
2018/0318585 A1 11/2018 Pfeifer
2018/0318586 A1 11/2018 Salazar
2020/0101290 A1* 4/2020 Rockley ............. A61N 1/36014
2020/0171307 A1 6/2020 Rockley et al.
2020/0324114 A1 10/2020 Chiapetta et al.
2022/0296899 A1 9/2022 Rockley et al.

FOREIGN PATENT DOCUMENTS

EP 1985332 A1 10/2008
GB 2246709 A 12/1992
WO 2006086452 A1 8/2006
WO 2013124141 A1 8/2013
WO 2015095257 A2 6/2015
WO 2016089751 A1 6/2016
WO 2017048731 A1 3/2017
WO 2017064500 A1 4/2017
WO 2018013835 A1 1/2018
WO 2018129351 A1 7/2018
WO 2018208009 A1 11/2018
WO 2020264263 A1 12/2020
WO 2021011255 A1 1/2021

OTHER PUBLICATIONS

2019 World Congress Eye and Chip Speaker Abstracts, pp. 20-54, 2019.

Gall et al; Alternating Current Stimulation for Vision Restoration after Optic Nerve Damage: A Randomized Clinical Trial, PLOS One, pp. 1-13, 2016, accessed Nov. 12, 2018.

Chow et al; "The Artificial Silicon Retina in Retinitis Pigmentosa Patients", Trans Am Ophthalmol Soc., vol. 108, pp. 120-154, 2010.

Dawson et al; "Improved Electrode for Electroretinography," Invest. Ophthalmol. Visual Sci. vol. 8, No. 9, pp. 988-991, Sep. 1979, accessed on May 2, 2019.

Diagnosys DTL Brochure, Diagnosys, LLC, 2016, Accessed Nov. 20, 2017.

DTL Installation, Diagnosys LLC, Accessed Oct. 6, 2020.

Bittner et al; "Longevity of Visual Improvements following Transcorneal Electrical Stimulation and Efficacy of Retreatment in Three Individuals with Retinitis Pigmentosa", Graefe's Archive for Clinical and Experimental Ophthalmology, 2017, Published online on Dec. 8, 2017.

H110002B Summary of Safety and Probable Benefits, Second Sight Medical Products Inc., issued Dec. 11, 2001.

H110002C Second Sight Manuals, Second Sight Medical Products Inc., 2013.

Naycheva et al; Phosphene Thresholds Elicited by Trasncorneal Electrical Stimulation in Healthy Subjects and Patients with Retinal Disease, Investigative Ophthamology and Visual Science, vol. 53, No. 12, pp. 7440-7448, 2012, accessed on Sep. 20, 2018.

Schatz et al; "Transcorneal Electrical Stimulation for Patients with Retinitis Pigmentosa: A Prospective Randomized, Sham-Controlled Follow-Up Study Over 1 Year", Investigative Ophthalmology and Visual Science, vol. 58, No. 1, pp. 257-269, 2017. Accessed on Sep. 25, 2018.

Scyfix SF700 Manual, Instructions for Use, pp. 1-28, Scyfix LLC. 2023. (No Year Given).

Stauffer et al; "Skin Conformal Polymer Electrodes for Clinical ECG and EEG Recordings," Advanced Healthcare Materials pp. 1-10, 2018.

Manthey et al; "Using Electrical Stimulation to Enhance the Efficacy of Cell Transplantation Therapies for Neurodegenerative Retinal Diseases: Concepts, Challenges, and Future Perspectives", Cell Transplantation, vol. 26, pp. 949-965, 2017.

Invitation To Pay Additional Fees dated Dec. 17, 2019 for International Application No. PCT/US2019/054028.

Invitation To Pay Additional Fees dated Feb. 14, 2020 for International Application No. PCT/US2019/063580.

International Search Report and Written Opinion dated Jul. 10, 2020 for International Application No. PCT/US2020/027438.

Krakova et al., "Spatial Differences in Corneal Electroretinogram Potentials Measured in Rat with a Contact Lens Electrode Array," Doc Ophthalmol vol. 129, pp. 151-166, 2014.

U.S. Appl. No. 17/782,100, filed Jun. 21, 2022.

* cited by examiner 10
20
12
16
22
18
14

22
12
13
24

SYSTEMS AND METHODS TO MANAGE MICROCURRENT THERAPY DOSE

CROSS REFERENCE TO RELATED APPLICATIONS

The present application claims the benefit of and priority to U.S. Provisional Patent Application 63/411,562, filed Sep. 29, 2022, titled SYSTEMS AND METHODS TO MANAGE MICROCURRENT THERAPY DOSE, the disclosure of which is incorporated herein by reference.

BACKGROUND

Electric fields have been applied non-invasively to the eye as a therapy for different retinal diseases including retinitis pigmentosa, macular degeneration, Stargardt's disease, glaucoma, and ischemic diseases. The mechanism of action is under investigation, and results have been mixed. New and alternative systems and methods to better quantify and/or calibrate therapy are desired.

OVERVIEW

The present inventors have recognized, among other things, that a problem to be solved is the need for new and/or alternative approaches to deliver therapy to the eye taking into account dosing challenges. While some therapies may be directed to the retina as a target, and the following discussion references the retina at various places, other eye-related targets may be considered as well, including the cornea, lens, vitreous, optic nerve, as well as other parts of the eye and its surroundings.

Electrical stimulation therapies for other indications (e.g., spinal cord stimulation for pain, or deep brain stimulation for movement disorders) have shown a dependency on proper dosing, and it is expected that the success and degree of benefit of non-invasive electrical eye therapy (NEET) would also be dose dependent. The relationships between gathered data and dose could be better controlled.

Non-invasive systems by definition do not include electrodes on or near the retina, and so the currents that pass through the retina are not measurable in this context. Often the amplitude of NEET is set as a percentage of the electrical phosphene threshold (EPT)—a surrogate for "current at the retina." However, it has been demonstrated that the EPT varies widely (multiple orders of magnitude) in the diseased eye (Naycheva et al., 2012), and current methods do not account for this fact.

As described more fully in the detailed description, the present disclosure provides new methods for calculating dosing, determining disease state, and otherwise configuring and/or calibrating NEET to the patient.

An illustrative, non-limiting example takes the form of an ophthalmic therapeutic system comprising therapy means for delivering electrical therapy; measuring means for measuring an energy change at the eye resulting from delivery of energy by the means for delivering electrical therapy; calculating means for calculating a desired dosage; control means for controlling the therapy means using data from the measuring means to deliver the desired dosage. Additionally or alternatively, the measuring means is configured to detect energy at the cornea. Additionally or alternatively, the calculating means is configured to: in a calibration step, determine a relationship between delivered electrical energy from the therapy means and a measured energy change at the eye; determine, using a patient's disease state, a target therapeutic dosage; combining the target therapeutic dosage and the relationship to determine the desired dosage for delivery by the therapy means. Another illustrative, non-limiting example takes the form of a method comprising: a) issuing an electrical therapy to the eye of a patient; b) measuring an energy change at the eye of the patient while issuing the electrical therapy of step a); c) repeating a) and b) to determine a phosphene threshold for the patient; d) estimating a disease state of the patient.

Another illustrative, non-limiting example takes the form of a method comprising: using a patient's known disease state, or lack of disease, estimating a phosphene threshold for the patient; a) issuing one or more first electrical therapy pulses to the eye of the patient; b) measuring an energy change at the eye of the patient while issuing the electrical therapy of step a); calculating a relationship between one or more features of the first electrical therapy pulses and an effect on the eye; issuing one or more second electrical therapy pulses to determine a functional phosphene threshold for the patient.

Additionally or alternatively, a method may include confirming the patient's known disease state in response to the functional phosphene threshold matching the estimated phosphene threshold. Additionally or alternatively, a method may include rejecting the patient's known disease state in response to the functional phosphene threshold not matching the estimated phosphene threshold. Additionally or alternatively, a method may include calculating a delivery relationship between therapy output and therapy at the eye of the patient; and determining a desired therapy output using the functional phosphene threshold, the patient's known disease state, and the delivery relationship. Additionally or alternatively, a method may include taking a measurement of corneal energy. Additionally or alternatively, a method may include delivering calibrated therapy pulses without measuring corneal energy.

Another illustrative, non-limiting example takes the form of an ophthalmic therapeutic system comprising: therapy means for delivering electrical therapy; measuring means for measuring an energy change at the eye resulting from delivery of energy by the means for delivering electrical therapy; calculating means for calculating a targeted dosage; control means for controlling the therapy means using data from the measuring means to deliver the targeted dosage to modulate a selected biomarker.

Another illustrative, non-limiting example takes the form of an ophthalmic therapeutic system comprising: therapy means for delivering electrical therapy; measuring means for measuring an energy change at the eye resulting from delivery of energy by the means for delivering electrical therapy; calculating means for calculating a targeted dosage; control means for controlling the therapy means using data from the measuring means to deliver the targeted dosage to modulate tissue at a selected region of the eye.

This overview is intended to provide an introduction to the subject matter of the present patent application. It is not intended to provide an exclusive or exhaustive explanation. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

In one embodiment, the dose is controlled by including in the estimate not only the electrical phosphene threshold EPT but also one or more attributes that affect the EPT. In one embodiment the attributes that affect the EPT include the eye disease of the person being treated, and the severity of the disease. In one embodiment, the severity of the disease is quantified from one or more diagnostics, such as visual acuity, or the electroretinagram (ERG). In one embodiment, the severity of the disease is described coarsely, such as mild, moderate, or severe. In one embodiment, the aforementioned information is used to estimate the dose in arbitrary units. An example of a candidate unit might be, the amount of current to elicit EPT in a healthy eye, and using the estimate model, the arbitrary units can be converted to a therapeutic setting in mA or volts (and perhaps pulse width and/or frequency). In one embodiment, a system receives the EPT data, and at least one attribute to which the EPT is sensitive (e.g., disease state), and uses that information to provide recommended settings. In one embodiment, a system also receives (e.g., manually input) a dose in arbitrary units (such as % EPT in a healthy eye) and determines an estimate of the desired stimulation amount, and delivers the estimated amount. In one embodiment, another arbitrary unit could be % or fraction to obtain a unit value of an electrical parameter (e.g., voltage, current, electric field strength, charge density, etc. at the cornea—which was measured during calibration in some use models.

In one embodiment, the aforementioned data is input by a clinician and fixed such that a patient or caregiver can take home a patient controller for delivering therapy. In one embodiment, the clinician inputs a range in which the patient is allowed to manipulate the stimulation amount at home. It is expected that when non-invasive stimulation is applied on the skin, the voltages and currents generated at the retina that comprise the actual dose (but that are not accessible for measurement) are related to voltages and currents generated at the anterior exposed portion of the eye (such as the cornea) and other nearby locations— and those voltages and currents are measurable.

Figure 1:
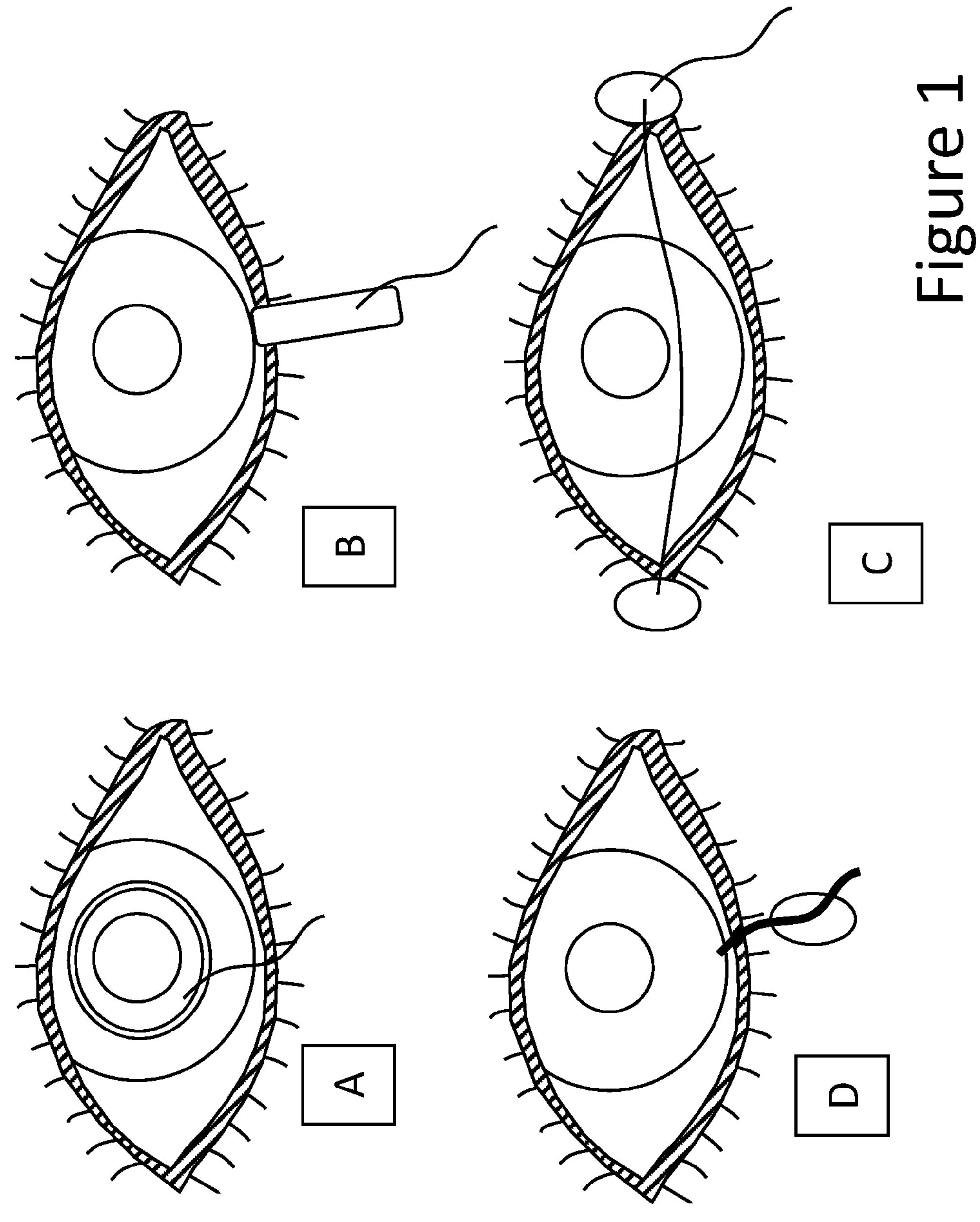
FIGS. 1-2 show illustrative electrodes and arrangements for measuring corneal energy.
Figure 2:
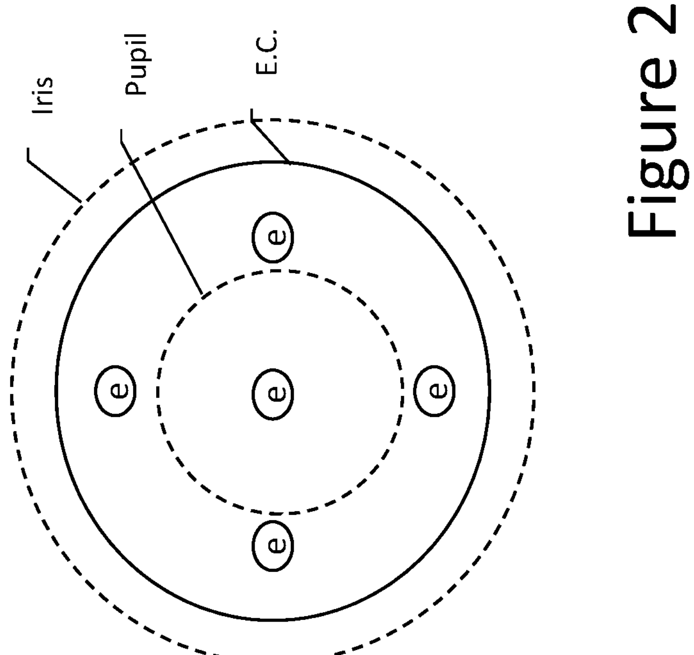

It is known that it is safe to place electrodes on the anterior portion of the exposed eye to measure the electroretinogram (ERG). Example placement of electrodes on the cornea are shown in FIGS. 1-2. In FIG. 1, starting with A, a wire attaches to a generally circular electrode array placed more or less over the iris and pupil. At B, electrodes can be carried on a flex circuit placed against the cornea at the lower eyelid. At C, a DTL electrode drapes across the cornea between two sticky pads placed on either side of the eye. At D, a sticky patch is used to hold an electrode-carrying wire at the lower eyelid, with the electrode contacting the cornea and/or palpebra. Turning to FIG. 2, an electrode array, with several electrodes e, is carried on a contact lens (electrode carrier, E.C.) applied to the cornea, over the iris and pupil. Other designs and/or positions can be used, as desired. ERG procedures rely on sensing the endogenous retinal activity.

In some examples of the present invention, contrary to ERG procedures, the measured voltages are not solely those due to endogenous retinal activity, but comprise voltages due to non-invasive stimulation with a NEET system. As an example, (1) one or more electrodes can be placed on the anterior eye and connected to a measurement system during a calibration phase; (2) the patient dons the NEET system; (3) stimulation is applied via the NEET system and measurements on the surface of the eye are made, and (4) the relationships between the amount of voltage or current applied by NEET and the voltage(s) impressed on the anterior eye are determined; (5) a therapy amplitude is determined based on that relationship. That is, the therapy amplitude in step (5) may provide a relationship between the output energy of the NEET system and energy that is received at the location of the measuring device, with energy received at the therapy target location (such as the maculae or fovea centralis) being still further inferred. Step (5) may include or may instead be a step of calculating a transfer function, which may be a simple, single variable, or may contemplate spatial variations, wherein the transfer function characterizes or models the flow of current from an electrode to the cornea, or to the retina, as desired.

If the sensing system has multiple electrodes, further examples may provide a mapping of the current on the cornea, allowing a better spatial understanding of where current is going when the patient receives the therapy. Doing so may allow the NEET system output electrode to be repositioned if, for example, it is desirable to redirect therapy spatially.

In addition to inferring voltage/current at a therapy target, it may also be that other parts of the eye contribute to therapy benefits. For example, improved vascular flow in the eye may aid in treatment of a disease, in addition to electrical stimulation having a benefit on a therapy target such as the maculae. Electrical parameters resulting from NEET therapy, measured at the cornea, can be used to better understand the effect of the electrical therapy on various structures in the eye.

In some examples, the assumption is made that the effects of energy at the retina vary with disease state, but the transmission of energy to the cornea or retina is less variable based on disease state. As such, energy transmission from the cornea to the retina for NEET may be modelled using, for example, bench studies and/or computer models. However, the effect of such energy on the retina, particularly with respect to phosphene thresholds, may be more variable. The transmission from the NEET system to the retina has two parts, the first of which (NEET to cornea) can be measured in a calibration procedure, and the second of which (cornea to retina) can be obtained from a model. An example of data collected in a bench setting and that supports calibration might be:

Measure corneal voltages due to outputs of the NEET system outputs. such that a relationship between electrical measurements at the cornea is understood for a given NEET configuration (electrode positions, stimulation parameters, etc.). The outputs used for calibration do not necessarily need to be the same, or even in the range of, parameters that are used for therapy. Parameters or models may be determined for healthy and/or unhealthy eyes, and/or measurements may be made for a specific patient to tailor that patient's therapy.

This relationship can then be used to help a patient that will be treated, since NEET configuration and corneal voltages are known, yielding understanding of how applied stimulus propagates to and/or through the eye.

A basic look-up or scaling method may be used to estimate a relationship between NEET system outputs and corneal voltages. More sophisticated models may be used instead. In some examples, spatial variations may be used, if desired, by, for example, having a NEET system that can applied stimuli using three or more electrodes, with a test or calibration stimulus delivery protocol including a pattern of use of the three or more electrodes that varies the spatial characteristics of the output therapy; as noted the measuring apparatus may be useful to sense the corneal voltages at a plurality of locations as well, allowing both the spatial variation of each pulse to be determined, as well as variations in signal propagation due to use of different electrodes at different positions. In another example, frequency variations may be used to determine variations in signal propagation due to changes in frequency, where the frequency content of the delivered signal may be varied (i.e., changing the frequency of a sinusoidal output, or changing the pulse width or pulse frequency of a pulsed output). In an example, a pattern of test signals varying in one or more of amplitude, frequency content, and/or spatial utilization may be generated to obtain transfer function information, with the transfer function information then used to customize therapy parameters, or pick ideal therapy parameters from a list/look-up table, for use with a patient.

It should be noted that some prior efforts have been focused mainly on determining EPT, rather than understanding electrical signal propagation. EPT may mix together both the electrical propagation and the particular patient's visual status, leaving therapy less specific/tailored than it otherwise could be. In an example, serial testing on a given patient may be useful to allow disease progression/status to be understood. For example, measuring corneal voltages during EPT testing can allow serial tests to be corrected for changes in electrical signal propagation to the cornea, which can vary due to electrode position, tissue interface impedance, patient hydration, etc., enabling the physician to better determine changes (or lack of changes) to the true EPT of the patient.

In another example, a calibration or test procedure may use a test apparatus having a plurality of therapy output electrodes thereon, to determine which electrode positions on or around the eye are advantageous for a given patient. In an example, a therapy delivery apparatus may then be customized to include electrodes at the advantageous locations. In an example, a therapy delivery apparatus with fewer electrodes than the test apparatus may be used, thus making the therapy delivery apparatus cheaper, lighter, or easier to use, than the test apparatus. In an example, a test apparatus may having a blacked out visual field to block light coming to the eye to minimize endogenous retinal activity due to incident light causing neural action potentials, to create a controlled baseline for the test procedure, where subsequently used therapy apparatuses may lack such a blacked out visual field.

In one embodiment, the voltages on/near the eye are measured as part of a patient specific calibration, and the calibration data is recorded in a component of the system.

In one embodiment, the NEET system delivers multiples pulses that result in measured voltages on/near the eye, and the calibration data is based on those voltages.

In one embodiment, multiple electrodes are placed on/near the eye simultaneously to enable additional processing steps. One example processing step includes calculating a voltage difference measured between two electrodes on/near the eye.

In one embodiment, the monopolar or multipolar impedance of electrodes placed on/near the eye is measured. In one embodiment, the impedance is used in the calibration process.

In one embodiment, the NEET system can be configured to measure the impedances of electrodes used in the calibration.

In one embodiment, the voltages on/near the eye are used to estimate an electrical dosage at the retina or another therapy target in an electrical unit (e.g., current, electric field magnitude, current density, etc.).

A first non-limiting illustrative example takes the form of an ophthalmic therapeutic system comprising: therapy means for delivering electrical therapy; measuring means for measuring an energy change at the eye resulting from delivery of energy by the means for delivering electrical therapy; calculating means for calculating a desired dosage; control means for controlling the therapy means using data from the measuring means to deliver the desired dosage. Therapy means may include a pulse generator, for example, as disclosed in any of U.S. Pat. No. 7,251,528, titled TREATMENT OF VISION DISORDERS USING ELECTRICAL, LIGHT, AND/OR SOUND ENERGY, US PG Pat. Pub. No. 2020-0324114, titled SYSTEMS AND INTERFACES FOR OCULAR THERAPY, US PG Pat. Pub. No. 2020-0101290 titled SYSTEMS AND METHODS FOR CONTROLLING ELECTRICAL MODULATION FOR VISION THERAPY, US PG Pat. Pub. No. 2020-0171307, titled HEAD WORN APPARATUSES FOR VISION THERAPY, U.S. patent application Ser. No. 16/900,115, filed Jun. 12, 2020, titled WEARABLE MEDICAL DEVICE, PCT Pat.

App. No. PCT/US2020/039776, filed Jun. 26, 2020, titled SYSTEMS AND INTERFACES FOR OCULAR THERAPY, and/or PCT Pat. App. No. PCT/US2020/041166, filed Jul. 8, 2020, titled OCULAR THERAPY MODES AND SYSTEMS, the disclosures of which are incorporated herein by reference. For example, therapy means may include an amplifier that provides a voltage output using one or more power supplies; the amplifier may be a discrete amplifier on a chip or may be constructed of several known electrical components including, for example, capacitors, transistors, resistors and/or inductors in suitable layout. Therapy mean may instead include a controlled current output including, for example, one or more selectable current mirrors or other layouts.

Measuring means may include electrodes positioned as shown, for example, in FIGS. 1-2, coupled to an electrical device having measuring circuitry therein such as filtering, amplifying, and/or quantifying circuitry including for example an analog-to-digital conversion circuit configured to convert an analog measurement signal to a digital value. Calculating means, as well as control means, may include any suitable logic and/or controller circuitry including, for example and without limitation, a microcontroller, microprocessor, state machine, and/or programmable gate array logic. The measuring, calculating and control means may each be incorporated together in a microcontroller or microprocessor, or state machine, using therewith or having therein signal processing circuitry. For microcontroller and/or microprocessor examples, and other examples as needed, suitable memory for storing therapy parameters, operational instruction sets, and various measured data and device history may be provided as well.

Additionally or alternatively to the first non-limiting illustrative example, the measuring means is configured to detect energy at the cornea. Additionally or alternatively to the first non-limiting illustrative example, the calculating means is configured to: in a calibration step, determine a relationship between delivered electrical energy from the therapy means and a measured energy change at the eye; determine, using a patient's disease state, a target therapeutic dosage; combining the target therapeutic dosage and the relationship of determine the desired dosage for delivery by the therapy means.

A second illustrative and non-limiting example takes the form of a method comprising: a) issuing an electrical therapy to the eye of a patient; b) measuring an energy change at the eye of the patient while issuing the electrical therapy of step a); c) repeating a) and b) to determine a phosphene threshold for the patient; d) estimating a disease state of the patient.

A third illustrative and non-limiting example takes the form of a method comprising: using a patient's known disease state, or lack of a disease at all, estimating a phosphene threshold for the patient; a) issuing one or more first electrical therapy pulses to the eye of the patient; b) measuring an energy change at the eye of the patient while issuing the electrical therapy of step a); calculating a relationship between one or more features of the first electrical therapy pulses and an effect on the eye; issuing one or more second electrical therapy pulses to determine a functional phosphene threshold for the patient.

Additionally or alternatively to the third illustrative and non-limiting example, the method may further comprise confirming the patient's known disease state in response to the functional phosphene threshold matching the estimated phosphene threshold. Additionally or alternatively to the third illustrative and non-limiting example, the method may further comprise rejecting a patient's known disease state in response to the functional phosphene threshold not matching the estimated phosphene threshold. Additionally or alternatively to the third illustrative and non-limiting example, the method may further comprise calculating a delivery relationship between therapy output and therapy at the eye of the patient; and determining a desired therapy output using the functional phosphene threshold, the patient's known disease state, and the delivery relationship.

Within the second or third illustrative and non-limiting examples, step b) may comprise taking a measurement of corneal energy. Further, the method may also comprise delivering calibrated therapy pulses without measuring corneal energy. That is, the calibrating steps at b) in the second or third illustrative and non-limiting examples may include placement of measuring electrodes on the cornea, if desired, and those measurement electrodes on the cornea may be used in a calibrating step and then removed or otherwise not used during subsequent therapy sessions. For example, a patient may be subject of the calibration steps using the corneal measurement electrodes during a periodic check-up (weekly, monthly, quarterly, annually, etc.), performed in-clinic for example, while using the device to perform therapy on a day-to-day basis.

Additional non-limiting examples may include a method and application of the method in a system for ophthalmic therapeutic delivery comprising: testing means for issuing one or more test electrical pulses to the eye of the patient, therapy means for delivering electrical therapy, measuring means for measuring an energy change at the eye resulting from delivery of the one or more test electrical pulses issued by the testing means, or the electrical therapy delivered by the therapy means for delivering electrical therapy; calculating means for calculating a target dosage to a location of the eye; control means for controlling the therapy means using data from the calculating means and the measuring means to deliver the target dosage. The system may include all components in one system or may be an assembly of subcomponents. In embodiments the therapeutic dosage delivered by the therapy means is determined by: a) issuing one or more test electrical pulses to the eye of the patient; b) measuring an energy change at the eye of the patient resulting from issuing the one or more test electrical pulses of a); c) calculating a relationship between one or more features of the test electrical pulses and the measured energy change at the eye to determine the target therapeutic dosage or dosage range; and d) delivering the target therapeutic dosage from the relationship calculated in c).

In some embodiments, the target therapeutic dosage delivered is determined for delivery to a specific location in the eye (e.g. retina, fovea, macula, pupil, vitreous, etc.) of the particular patient. The target therapeutic dosage may be calculated based on anatomical and physiological characteristics of the particular patient, phosphene response from issuing the one or more test electrical pulses and/or other information, including, for example, information on the location of one or more electrodes applied to the patient for delivering one or more of the test electrical pulses or the therapeutic dosage. In these embodiments the calculation of a relationship of step c) is determined by comparing the energy change at the eye from step b) to a reference library of dosage settings to deliver a targeted energy to the particular location of the eye based on the energy change from step b). In these examples the reference library may be built from actual or computational models predicting the amount of energy that will be delivered to a determined location in the eye from values determined from the measured energy change resulting from issuing the one or more first electrical pulses to the eye of the patient.

As an alternative to the use of a reference library, step c) may include reference to one or more of:

A general anatomic model

An anatomic model specific to the patient such as developed by use of additional imaging studies (x-ray, MRI, etc.)

A model based on disease state of the patient

Such models may be used to determine or estimate energy transference to a therapeutic target from the electrodes used to issue any of therapeutic or test electrical pulses. Imaging studies may further include the use of functional MRI in which stimulus is provided to the eye in any selected form (optical, electric, mechanical) and neural response is observed by determining minute changes in blood flow. The procedure may include, in an example, using patient-specific data, identifying a therapeutic target (spatial) in the patient. Using test pulses and a corneal measurement, a model of electrical flow, such as a transfer function, from electrodes to a reference position in the patient (the cornea) is determined. Again, using patient specific data (or alternatively, a physiological model), electrical flow from the reference position in the patient (the cornea) to the spatial therapeutic target is modeled/estimated. Finally, using the patient's disease state, and/or using patient feedback such as phosphene threshold, therapy settings can be calculated.

In another example, the corneal electrical measurement may be used to determine an evoked response to the delivered test pulses, or to delivered therapy pulses. For example, an electrical test or therapy pulse may be delivered, and a sensing circuit may be configured to sense for a response from the patient's tissue over a period of time subsequent to the electrical test or therapy pulse.

Systems for measuring electrical potentials measured at the cornea are known and include for example systems and methods disclosed in Krakova, Y. et. al., SPATIAL DIFFERENCES IN CORNEAL ELECTRORETINOGRAM POTENTIALS MEASURE IN THE RAT WITH CONTACT LENS ELECTRODE ARRAY, Doc Ophthalmol. (2014) 129:1511-166, the entire disclosure of which is incorporated herein by reference. However, in contrast to use of current systems for measuring electrical potentials induced at the cornea after light stimulation of the eye, the invention is directed to measuring electrical potentials at the cornea induced by delivering energy through electrodes positioned external to the eye at locations including, for example, the forehead region, the mastoid, periorbital regions superior, inferior, lateral or medial to the eye, cheek region or other regions of the face, head or body.

In some embodiments, the measuring means for measuring an energy change at the eye comprises one or more sensing electrodes applied to the cornea. In embodiments one, two or more electrodes may be used mounted to a continuous structure such as lens that aligns with the contours of the cornea. In embodiments at least 6, at least 12, at least 24, or at least 36 or more sensing electrodes are positioned at multiple locations around the lens to facilitate characterization of measured energy at spatial distances around the surface of the cornea or perimeter regions of the surface of the eye. For example, an array as shown in FIG. 2 may include a number of additional electrodes located generally near the pupil and/or irirs. In another example, again using FIG. 2, the electrode carrier, E.C., may be larger, relative to the eye, than that shown, so that not only the pupil and iris are covered, but also sclera away from the iris.

It will be appreciated that the energy measured may include information from multiple energy sources induced by the test electrical pulses or therapeutic or electrical therapy. Such information may include, for example, basal energy transmitted from non-electrically induced regions of the eye, energy transmitted from the retina or other regions of the eye that are induced by a test electrical pulse or electrical therapy, energy transmitted from other parts of the body that are induced by a test electrical pulse or electrical therapy. Filtering algorithms may be used to determine the measured energy resulting from the particular region of the eye such as the retina generally or the macula, the fovea or other regions of the eye.

Thus, while much prior work has relied on phosphene elicitation as a surrogate indicator of energy delivered to the retina, such information lacks quantification of the actual amount of energy delivered to the retina as it relies on the inter-patient and intra-patient variability of functional status of the retina. This short coming of relying solely on the qualitative nature of phosphene elicitation to determine an effective therapeutic dose becomes an obstacle for optimal clinical outcomes as more and more scientific literature is elucidating that specific energy characteristics (e.g. waveform, amplitude, pulse width, frequency, etc.) determines the specific biomarkers or biomolecules (e.g. proteins, cytokines, lipids, neurotrophic agents, etc.) that may be selectively modulated with specific targeted therapeutic dosages.

In any of these examples, subjective or objective feedback from the patient may also be used as a control signal for optimizing dose. Sometimes the patients have anecdotes and experiences that are not readily quantifiable by standard clinical metrics, but that are meaningful to them. Automated dosing algorithms may be configured to respond to patient inputs by increasing or decreasing any of amplitude, pulse width, pulse frequency, therapy session duration, therapy session frequency, or other characteristics, based on such inputs.

Another illustrative and non-limiting example takes the form of a method of tracking a patient's disease state. A first phosphene threshold for the patient is measured using a phosphene threshold test at a first point in time. At a later point in time, a second phosphene threshold for the patient is measured. Using as another input the patient's known disease, the progression (or reversal) of disease state can then be inferred by comparing the first and second phosphene thresholds. To enhance accuracy of a testing series, the phosphene threshold tests may be performed with corneal electrodes present, removing error that may be associated with electrode position during NEET therapy delivery, changes in patient skin, dampness, electrode-skin interface characteristics, etc. Such corneal electrodes may be used in an example to measure EPT. Within a similar paradigm, comparison of the first and second phosphene threshold tests may be used to estimate the effectiveness of a dose, and then used as an input to refine and optimize the dose for a given patient. For example, for a given patient, expected disease progress without therapy may be estimated, and used in a model to determine what the expected change in phosphene threshold for the patient would be without therapy. Comparing actual with expected phosphene threshold tests would inform therapy determinations.

Figures 3, 4:
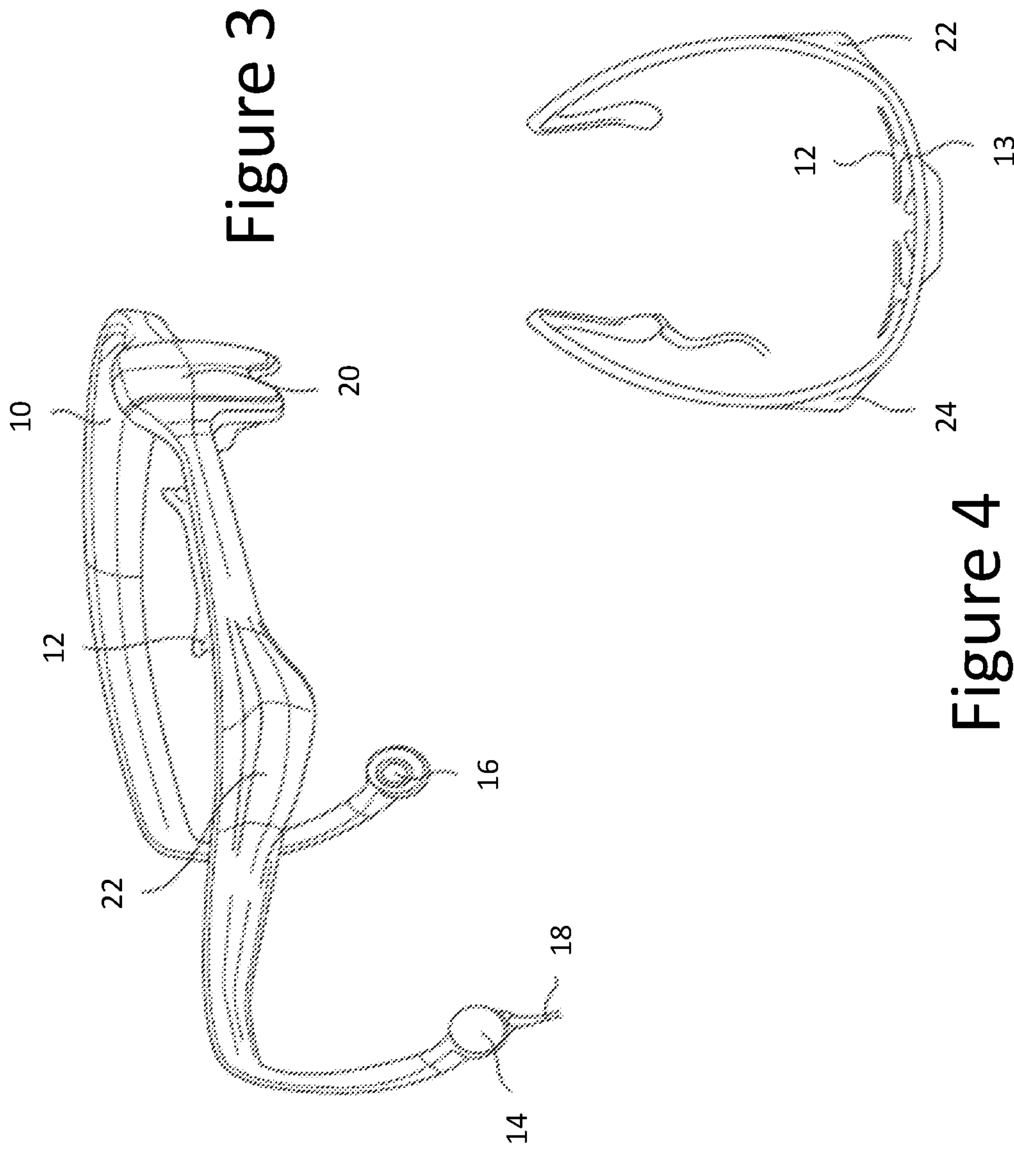
FIGS. 3-4 shows an illustrative therapy system.

FIGS. 3-4 show an illustrative therapy apparatus in the form of a frame 10 wearable on the head of a user. The frame 10 includes an electrode carrier 12 for placement against one or more of the forehead, upper eyelid, lower eyelid, or cheek of the user, where the example shown in FIG. 3 may generally place an electrode on the forehead or upper eyelid. The electrode carrier 12 may be coupled to the frame 10 with an adjustable arm 13, as shown in FIG. 4, allowing the user to don the frame 10, and then adjust positioning of the electrode carrier to a preferred position, such as on the forehead, upper or lower eyelid, cheek, nose, or on the eye itself, or on the conjunctiva, as suitable to the particular implementation.

In other examples, the electrode carrier 12 may be positioned differently; a range of placements and designs are shown in of U.S. Pat. No. 7,251,528, titled TREATMENT OF VISION DISORDERS USING ELECTRICAL, LIGHT, AND/OR SOUND ENERGY, US PG Pat. Pub. No. 2020-0324114, titled SYSTEMS AND INTERFACES FOR OCULAR THERAPY, US PG Pat. Pub. No. 2020-0101290 titled SYSTEMS AND METHODS FOR CONTROLLING ELECTRICAL MODULATION FOR VISION THERAPY, US PG Pat. Pub. No. 2020-0171307, titled HEAD WORN APPARATUSES FOR VISION THERAPY, U.S. patent application Ser. No. 16/900,115, filed Jun. 12, 2020, titled WEARABLE MEDICAL DEVICE, PCT Pat. App. No. PCT/US2020/039776, filed Jun. 26, 2020, titled SYSTEMS AND INTERFACES FOR OCULAR THERAPY, and/or PCT Pat. App. No. PCT/US2020/041166, filed Jul. 8, 2020, titled OCULAR THERAPY MODES AND SYSTEMS, the disclosures of which are incorporated herein by reference.

The frame 10 also includes earpieces 14 and 16, which may, as shown at 16, include or be attached to additional electrodes useable for therapy delivery and/or sensing, as noted and described in the above identified, incorporated by reference, patents and applications. The frame 10 may be coupled to a cord 18, which can carry or attach to another electrode, such as a return or indifferent electrode placed on the torso or a limb, such as the arm, of a user. The cord 18 may instead couple to a remote control that a user can hold to control operation of the system, such as to turn therapy on/off, to select modes of sensing, testing, therapy, etc., or to change therapy parameters. The cord 18 may in some examples couple to a pulse generator that includes a power source and sensing, control, and/or therapy output circuitry. Rather than a separate pulse generator, power source, control, sensing and therapy output circuitry may be carried on the frame itself, such as in an enlarged section shown at 22 in FIG. 3, or portion 22 and 24 as shown in FIG. 4. The cord 18 may be omitted, if desired.

In some further examples the system, including the frame 10 and electrode carrier 12, along with a remote control or patient controller (wired or wireless) may also take the form as shown in U.S. Provisional Patent Application 63/418,375, filed Oct. 21, 2022, titled OCULAR DEVICES AND CONTROLLER INTERFACES FOR OCULAR THERAPY, the disclosure of which is incorporated herein by reference.

The output circuitry may be configured to issue therapy pulses of a wide-ranging variety of types. For example, the therapy parameters disclosed in any of the above identified, incorporated by reference patents and applications may be used. In some examples, multi-phase or multi-mode stimulation may be performed. Certain specific examples follow.

Figure 5:
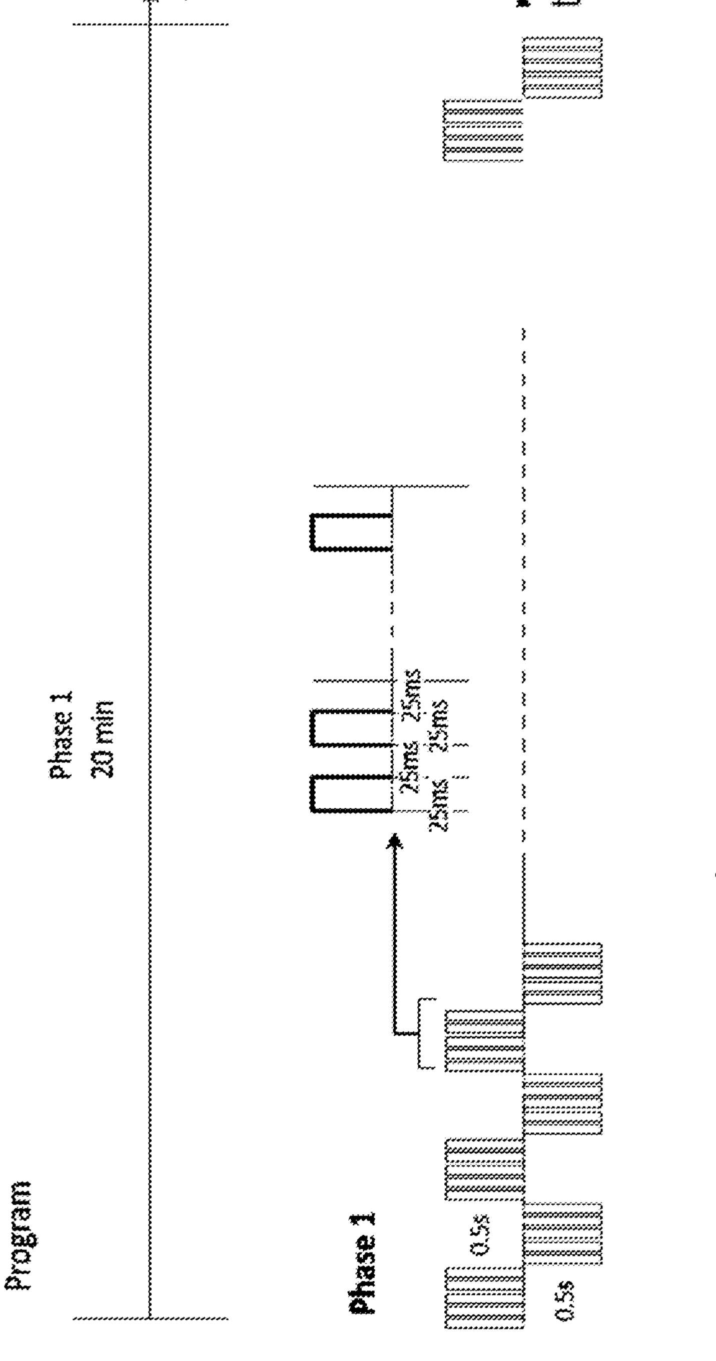
FIGS. 5-6 show illustrative therapy protocols.

FIG. 5 shows an illustrative 20 Hz Fixed program. Here, therapy has a single phase lasting, illustratively, for 20 minutes (longer or shorter may be used, anywhere from 1 minute to 100 minutes, or more or less as desired). The therapy output is delivered at 20 Hz (1/20 of a second, or 50 milliseconds (ms)), by issuing a 25 ms duration pulse, followed by 25 ms of quiescent time. Every 500 ms, the output polarity switches. The amplitude of therapy can be fixed throughout the duration of the single phase, though in other examples, amplitude may vary, such as by including an initial ramp in which the amplitude starts near zero, and then raises to the selected therapy amplitude over the course of several pulses. In another example, the first pulse of each 500 ms block of pulses at a given polarity can be reduced in amplitude compared to other pulses in the block, such as by using a reduced amplitude in the range of about 10% to about 90%. The nominal amplitude for therapy pulses may be selected to be above, at, or below a phosphene threshold for the patient, for example. In other examples, therapy amplitude may be selected using the above described methods in which corneal voltages, whether derived from the therapy output or indicating an evoked response, are measured and used to set therapy nominal amplitude.

Figure 6:
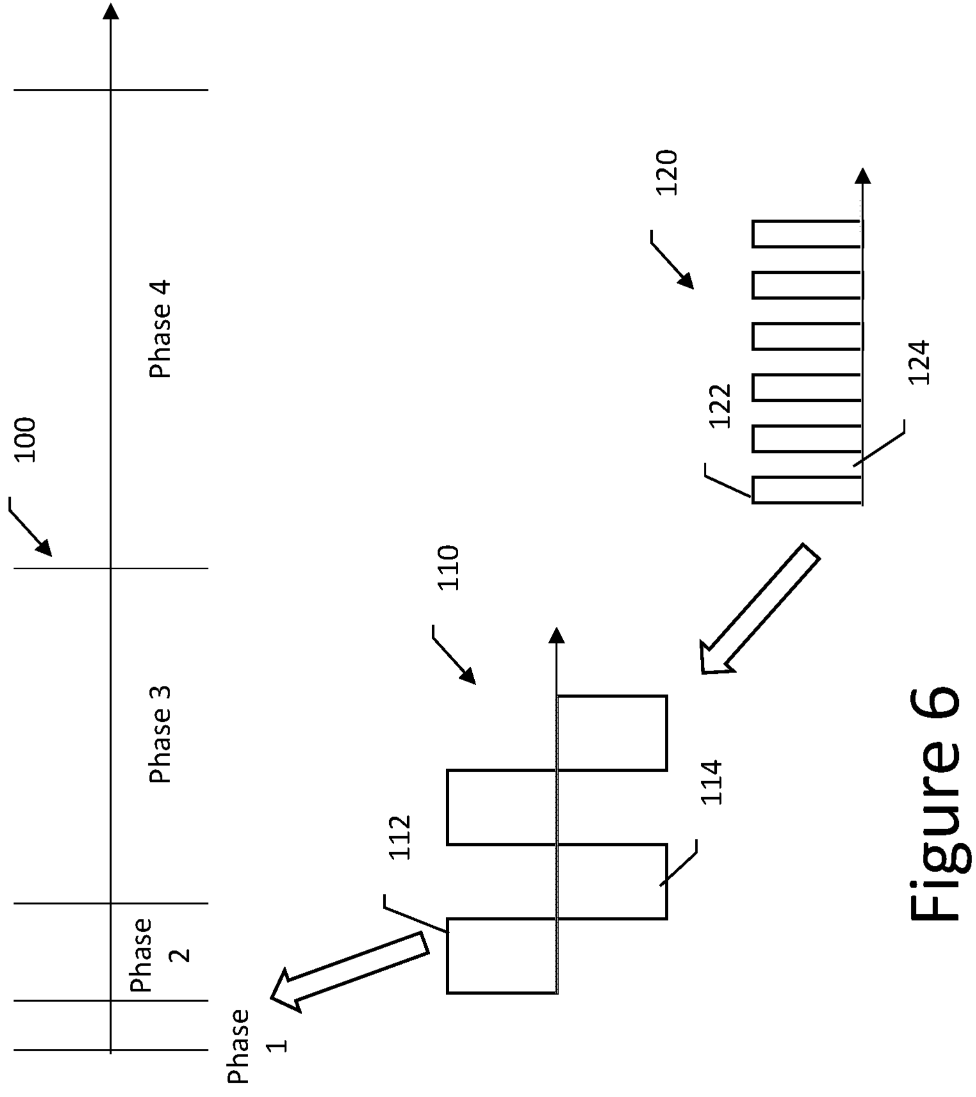

FIG. 6 illustrates a multi-phase stimulation pattern. Here, as shown at 100, a series of phases of therapy are delivered. Each phase includes a series of alternating blocks of therapy output, as shown at 110, where blocks of therapy are issued with alternating polarity from one block 112 to the next block 114. Within each block 112, 114, a therapy pattern as shown at 120 is delivered, with pulses 122 having a fixed duration, followed by a quiescent period 124. In an example, each phase is used for a period of time, and each phase has a different definition of one or more of the duration of blocks 112/114, or pulse durations 122. Amplitude may be fixed throughout, or amplitude may vary from one phase to another, or within a phase, or from one block 112 to the next 114, or within a block from one pulse 112 to another, as desired. In an example, the phases may be:

Phase 1 lasts for 1 minute, with 500 ms blocks 112/114 alternating polarity, having 2 ms pulses 122 separated by 2 ms quiescent periods 124.

Phase 2 lasts for 2 minutes, with 500 ms blocks 112/114 alternating polarity, having 20 ms pulses 122 separated by 20 ms quiescent periods 124.

Phase 3 lasts for 7 minutes, with 500 ms blocks 112/114 alternating polarity, having 50 ms pulses 122 separated by 50 ms quiescent periods 124.

Phase 4 lasts for 10 minutes, with 500 ms blocks 112/114 alternating polarity, having 2 seconds pulses 122 separated by 2 second quiescent periods 124. Phase 4 may alternatively be described as having issuing a DC output for 500 ms, in alternating polarity for 2 seconds, followed by 2 seconds quiescent period.

An alternative example uses Phases 1-3, but omits phase 4. Still other examples may omit any one of the phases, such as using phases 1, 3 and 4, or phases 1, 2 and 4, or phases 2, 3 and 4. Still other examples may use any selected two of the above phases, such as phases 1 and 2, or phases 1 and 3, or phases 1 and 4, or phases 2 and 3, or phases 2 and 4, or phases 3 and 4. Still other examples may reorder the above phases, or use a given phase more than once within a phase pattern. It may be noted that the pulse widths used are longer than those used, for example, with various neuromodulation systems such as Deep Brain Stimulation (DBS), where DBS systems may be, for example, limited to a pulse width of about 500 microseconds or less.

It should be noted that the above examples are delivered using the signals as described, without the use of a carrier signal. In other examples a carrier signal may be used in defining these therapy patterns, such as by using the above examples as the envelope in which a signal (square wave, sinusoid, etc.) having a frequency in the kilohertz (kHz) range (such as 0.1 to 100 kHz, or higher, if desired) is delivered. For example, a 10 kHz square wave or sinusoidal carrier signal may be used. Such a carrier signal may, in some examples, reduce electrode-skin interface impedance.

Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls. In this document, the terms "a" or "an" are used, as is common in patent documents, to include one or more than one, independent of any other instances or usages of "at least one" or "one or more." Moreover, in the claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic or optical disks, magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims.

Also, in the above Detailed Description, various features may be grouped together to streamline the disclosure. This should not be interpreted as intending that an unclaimed disclosed feature is essential to any claim. Rather, innovative subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the protection should be determined with reference to the appended claims, along with the full scope of equivalents to which such claims are entitled.

What is claimed is:

1. An ophthalmic therapeutic system for treating an eye of a patient, comprising:

therapy circuitry for delivering electrical therapy, comprising a pulse generator configured to generate repeated electrical pulses;

a sensing circuit for measuring an energy change at the eye resulting from delivery of energy by the therapy circuitry; and a controller configured to:

obtain the measured energy change from the sensing circuit;

calculate a desired therapy dosage; and control the therapy circuitry to deliver the desired dosage to the eye of the patient, wherein the controller is configured to calculate the desired therapy voltage by:

in a calibration step, determining a relationship between delivered electrical energy from the therapy circuitry and the measured energy change;

determining, using a patient's disease state, a target therapeutic dosage; and combining the target therapeutic dosage and the relationship to determine the desired dosage for delivery by the therapy circuitry, and wherein the target therapeutic dosage is defined as a therapy voltage to be delivered to a retina of the eye, and the relationship is defined as energy received at the cornea from energy output by the therapy circuitry.

2. The system of claim 1, further comprising a plurality of electrodes on an electrode carrier configured to be located at the patient's eye, wherein the therapy circuitry and sensing circuitry are both electrically coupled to the plurality of electrodes.

3. The system of claim 1, wherein the controller is configured to combine the target therapeutic dosage and the relationship using a model for propagation of energy through eye tissue.

4. A method comprising:

using a patient's known disease state, or lack of disease, estimating a phosphene threshold for the patient;

a) issuing one or more first electrical therapy pulses to the eye of the patient;

b) measuring an energy change at the eye of the patient while issuing the electrical therapy of step a), wherein step b) comprises taking a measurement of corneal energy;

calculating a relationship between one or more features of the first electrical therapy pulses and an effect on the eye;

issuing one or more second electrical therapy pulses to determine a functional phosphene threshold for the patient.

5. The method of claim 4, further comprising confirming the patient's known disease state in response to the functional phosphene threshold matching the estimated phosphene threshold.

6. The method of claim 4, further comprising rejecting the patient's known disease state in response to the functional phosphene threshold not matching the estimated phosphene threshold.

7. The method of claim 4, further comprising:

calculating a delivery relationship between therapy output and therapy at the eye of the patient; and determining a desired therapy output using the functional phosphene threshold, the patient's known disease state, and the delivery relationship.

8. The method of claim 7, further comprising delivering calibrated therapy pulses without measuring corneal energy as part of delivering the calibrated therapy pulses.

9. A system comprising each of a pulse generator, sensing and/or measuring circuitry, and a plurality of electrodes for placement on a patient near the eye coupled to the pulse generator and sensing and/or measuring circuitry, also including a controller configured to perform the method of claim 4 using the pulse generator, sensing and/or measuring circuitry, and the plurality of electrodes.

* * * * *